United States Patent
Hoskuldsson et al.

(10) Patent No.: US 10,588,550 B2
(45) Date of Patent: Mar. 17, 2020

(54) METHOD, APPARATUS, AND SYSTEM FOR MEASURING RESPIRATORY EFFORT

(71) Applicant: NOX MEDICAL, Reykjavik (IS)

(72) Inventors: Sveinbjorn Hoskuldsson, Reykjavik (IS); Haraldur Tomas Hallgrimsson, Hafnarfjodur (IS); Gudjon Teitur Sigurdarson, Reykjavik (IS)

(73) Assignee: NOX MEDICAL, Reykjavik (IS)

( * ) Notice: Subject to any disclaimer, the term of this patent is extended or adjusted under 35 U.S.C. 154(b) by 1188 days.

(21) Appl. No.: 14/535,093

(22) Filed: Nov. 6, 2014

(65) Prior Publication Data

US 2015/0126879 A1    May 7, 2015

(30) Foreign Application Priority Data

Nov. 6, 2013   (IS) .......................................... 050066

(51) Int. Cl.
*A61B 5/113*    (2006.01)
*A61B 5/00*    (2006.01)
(Continued)

(52) U.S. Cl.
CPC .......... *A61B 5/1135* (2013.01); *A61B 5/0205* (2013.01); *A61B 5/0535* (2013.01);
(Continued)

(58) Field of Classification Search
CPC .... A61B 5/1135; A61B 5/0535; A61B 5/0809
See application file for complete search history.

(56) References Cited

U.S. PATENT DOCUMENTS

| 937,130 | A | 10/1909 | Williams |
|---|---|---|---|
| 1,001,054 | A | 8/1911 | Lawrence |

(Continued)

FOREIGN PATENT DOCUMENTS

| DE | 199 41 500 A1 | 3/2001 |
|---|---|---|
| DE | 19941500 A1 | 3/2001 |

(Continued)

OTHER PUBLICATIONS

Sackner et al. "Calibration of respiratory inductive plethysmograph during natural breathing." J Appl Physiol (1985). Jan. 1989;66(1):410-2.*

(Continued)

*Primary Examiner* — Meredith Weare
(74) *Attorney, Agent, or Firm* — Workman Nydegger

(57) ABSTRACT

A method, apparatus, and system for measuring respiratory effort of a subject are provided. A thorax effort signal and an abdomen effort signal are obtained. The thorax effort signal and the abdomen effort signal are each divided into a volume-contributing component of the respiratory effort and a paradox component. The paradox component represents a non-volume-contributing component of the respiratory effort. The abdomen paradox component is negatively proportional to the thoracic paradox component. The thorax effort signal or the abdomen effort signal or both are weighted by a weight factor to obtain a volume-proportional signal. The volume-proportional signal is proportional to the actual respiratory volume of the respiratory effort. A calibration factor for calibrating the thorax effort signal and the abdomen effort signal is obtained by optimizing the weight factor by minimizing thoracic paradox component and the abdomen paradox component.

20 Claims, 3 Drawing Sheets

(51) Int. Cl.
  *A61B 5/0205* (2006.01)
  *A61B 5/08* (2006.01)
  *A61B 5/053* (2006.01)
  *A61B 5/087* (2006.01)
  *A61B 5/091* (2006.01)
  *A61B 5/024* (2006.01)

(52) U.S. Cl.
  CPC .......... *A61B 5/0806* (2013.01); *A61B 5/7278* (2013.01); *A61B 5/024* (2013.01); *A61B 5/087* (2013.01); *A61B 5/0809* (2013.01); *A61B 5/091* (2013.01); *A61B 2560/0223* (2013.01)

(56) References Cited

U.S. PATENT DOCUMENTS

| | | | |
|---|---|---|---|
| 1,115,459 A | 10/1914 | Abizaid | |
| 1,193,050 A | 8/1916 | Orewiler | |
| 2,305,277 A | 12/1942 | Sloane et al. | |
| 2,649,573 A | 8/1953 | Goldberg et al. | |
| 2,667,159 A | 1/1954 | Goldberg et al. | |
| 3,092,759 A | 6/1963 | Sommer | |
| 3,347,223 A | 10/1967 | Pacela | |
| 3,500,823 A | 3/1970 | Richardson et al. | |
| 3,560,845 A | 2/1971 | Goldber et al. | |
| 3,685,105 A | 8/1972 | Carlile et al. | |
| 4,308,872 A | 1/1982 | Watson et al. | |
| 4,373,534 A | 2/1983 | Watson | |
| 4,430,777 A | 2/1984 | Takeda | |
| 4,671,591 A | 6/1987 | Archer | |
| 4,777,962 A | 10/1988 | Watson et al. | |
| 4,807,640 A | 2/1989 | Watson et al. | |
| 4,815,473 A | 3/1989 | Watson et al. | |
| 4,817,625 A | 4/1989 | Miles | |
| 4,832,608 A | 5/1989 | Kroll | |
| 4,834,109 A | 5/1989 | Watson | |
| 4,842,557 A | 6/1989 | Muz | |
| 5,301,678 A | 4/1994 | Watson et al. | |
| 5,326,272 A | 7/1994 | Harhen et al. | |
| 5,331,968 A | 7/1994 | Williams et al. | |
| 5,348,008 A | 9/1994 | Bornn et al. | |
| 5,353,793 A | 10/1994 | Bornn | |
| 5,543,012 A | 8/1996 | Watson et al. | |
| 6,148,486 A | 11/2000 | Uehara et al. | |
| 6,327,486 B1 | 12/2001 | Nissila et al. | |
| 6,341,504 B1 | 1/2002 | Istook | |
| 6,413,225 B1 | 6/2002 | Sackner et al. | |
| 6,461,307 B1 | 10/2002 | Kristbjarnarson et al. | |
| 6,807,438 B1 | 10/2004 | Brun Del Re et al. | |
| 6,993,378 B2 | 1/2006 | Wiederhold et al. | |
| 7,171,265 B2 | 1/2007 | Hoium et al. | |
| 7,267,652 B2 | 9/2007 | Coyle et al. | |
| 7,593,767 B1 | 9/2009 | Modarres | |
| 7,604,603 B2 | 10/2009 | Sackner et al. | |
| 7,670,295 B2 | 3/2010 | Sackner et al. | |
| 7,727,161 B2 | 6/2010 | Coyle et al. | |
| 7,762,953 B2 | 7/2010 | Derchak et al. | |
| 7,819,710 B2 | 10/2010 | McIntire et al. | |
| 7,878,979 B2 | 2/2011 | Derchak | |
| 7,914,350 B1 | 3/2011 | Bozich et al. | |
| 8,025,539 B2 | 9/2011 | Hermannsson | |
| 8,033,996 B2 | 10/2011 | Behar | |
| 8,034,001 B2 | 10/2011 | Gal | |
| 8,052,612 B2 | 11/2011 | Tang et al. | |
| 8,137,270 B2 | 3/2012 | Keenan et al. | |
| 8,165,654 B2 | 4/2012 | Tang et al. | |
| 8,177,724 B2 | 5/2012 | Derchak et al. | |
| 8,193,821 B2 | 6/2012 | Mueller et al. | |
| 8,251,736 B2 | 8/2012 | McIntire et al. | |
| 8,475,387 B2 | 7/2013 | Derchak et al. | |
| 8,579,794 B2 | 11/2013 | Henke | |
| 8,628,480 B2 | 1/2014 | Derchak | |
| 8,679,012 B1 | 3/2014 | Kayyali | |
| 8,762,733 B2 | 6/2014 | Derchak et al. | |
| 8,777,868 B2 | 7/2014 | Gal | |
| 8,790,255 B2 | 7/2014 | Behar | |
| 8,790,272 B2 | 7/2014 | Sackner et al. | |
| 9,059,532 B2 | 6/2015 | Hermannsson | |
| 9,192,316 B2 | 11/2015 | Hoskuldsson et al. | |
| 2002/0032386 A1 | 3/2002 | Sackner et al. | |
| 2002/0032388 A1 | 3/2002 | Kristbjarnarson et al. | |
| 2002/0120207 A1* | 8/2002 | Hoffman | A61B 5/0809 600/538 |
| 2003/0135127 A1 | 7/2003 | Sackner et al. | |
| 2005/0054941 A1 | 3/2005 | Ting et al. | |
| 2005/0119586 A1 | 6/2005 | Coyle et al. | |
| 2006/0122528 A1 | 6/2006 | Gal | |
| 2006/0258948 A1 | 11/2006 | Linville | |
| 2006/0282001 A1 | 12/2006 | Noel et al. | |
| 2007/0167089 A1 | 7/2007 | Gobron et al. | |
| 2009/0259135 A1 | 10/2009 | Stasz | |
| 2010/0060300 A1 | 3/2010 | Muller et al. | |
| 2010/0075527 A1 | 3/2010 | McIntire et al. | |
| 2010/0075549 A1 | 3/2010 | McIntire et al. | |
| 2010/0297868 A1 | 11/2010 | Hermannsson | |
| 2011/0151728 A1 | 6/2011 | Astola | |
| 2011/0248729 A2 | 10/2011 | Mueler et al. | |
| 2012/0101357 A1 | 4/2012 | Hoskuldsson et al. | |
| 2014/0323847 A1 | 10/2014 | Mccool | |
| 2015/0280348 A1 | 10/2015 | Hermannsson | |
| 2016/0135715 A1 | 5/2016 | Seppä et al. | |
| 2017/0143206 A1 | 5/2017 | Kotz et al. | |
| 2018/0049678 A1 | 2/2018 | Hoskuldsson et al. | |

FOREIGN PATENT DOCUMENTS

| | | | |
|---|---|---|---|
| EP | 2324760 | A2 | 5/2011 |
| EP | 2324761 | A2 | 5/2011 |
| EP | 2417905 | A1 | 2/2012 |
| EP | 2484276 | A2 | 8/2012 |
| EP | 2484277 | A2 | 8/2012 |
| EP | 2484278 | A3 | 8/2012 |
| EP | 2508123 | A1 | 10/2012 |
| EP | 2508124 | A2 | 10/2012 |
| EP | 2584962 | A2 | 5/2013 |
| EP | 2589335 | A2 | 5/2013 |
| WO | 02/02013 | A1 | 1/2002 |
| WO | 02/080761 | A2 | 10/2002 |
| WO | 2006024024 | A2 | 3/2006 |
| WO | 2006/066566 | A2 | 6/2006 |
| WO | 2008102140 | A1 | 8/2008 |
| WO | D071077-002 | | 10/2008 |
| WO | 20080133394 | A1 | 11/2008 |
| WO | 2011029136 | A1 | 3/2011 |
| WO | 2018033889 | A1 | 2/2018 |

OTHER PUBLICATIONS

Cohen, K.P. et al., "Breath Detection Using a Fuzzy Neural Network and Sensor Fusion", 1995 International Conference on Acoustics, Speech, and Signal Processing, May 9-12, 1995, vol. 5, pp. 3491-3494.

Stromberg, N.O.T., "Error analysis of a natural breathing calibration method for respiratory inductive plethysmography", Medical & Biological Engineering & Computing 2001, vol. 39, No. 3, May 1, 2001, pp. 310-314.

Cohen, Kevin P et al., "Comparison of Impedance and Inductance Ventilation Sensors on Adults During Breathing, Motion, and Simulated Airway Obstruction", IEEE Transactions on Biomedical Engineering, vol. 44, No. 7, Jul. 1, 1997, pp. 555-565.

International Search Report from Corresponding PCT Application No. PCT/IB2014/002760, dated Mar. 27, 2015.

Attachment A, to Natus' Third Supplemental Invalidity and Unenforceability Contentions, U.S. Pat. No. 9,059,532, *Nox Medical Ehf.* v. *Natus Neurology, Inc.*, Civil Action No. 15-cv-00709-RGA (D. Del), 63 Pages.

International Search Report from PCT Application No. PCT/IS2011/050010, dated Feb. 29, 2012.

International Search Report from PCT Application No. PCT/IB2014/002760, dated Mar. 27, 2015.

(56) References Cited

OTHER PUBLICATIONS

International Preliminary Report on Patentability from PCT Application No. PCT/IB2014/002760, dated May 10, 2016.
"Opinion Regarding European Patent, 2584962", Kilbun & Strode, Mar. 11, 2015, 14 Pages.
Notice of Appeal, Western High Court, Cephalon A/S, VS, Nox Medical Ehf, Mar. 9, 2015, 10 Pages.
"Defendant's Preliminary Invalidity and Unenforceability Contentions," Nox Medical EHF v. Natus Neurology Inc., Defendants, Civil Action No. 1:15-cv-00709-RGA, In the United States District Court for the District of Delaware, Apr. 15, 2016, 117 Pages.
"Defendant's First Supplemental Invalidity and Unenforceability Contentions," Nox Medical EHF v. Natus Neurology Inc., Defendants, Civil Action No. 1:15-cv-00709-RGA, In the United States District Court for the District of Delaware, Dec. 1, 2016, 3 Pages.
"Defendant's Second Supplemental Invalidity and Unenforceability Contentions," Nox Medical EHF v. Natus Neurology Inc., Defendants, Civil Action No. 1:15-cv-00709-RGA, In the United States District Court for the District of Delaware, 2009, 59 Pages.
"Defendant's Third Supplemental Invalidity and Unenforceability Contentions," Nox Medical EHF v. Natus Neurology Inc., Civil Action No. 1:15-cv-00709-RGA, In the United States District Court for The District of Delaware, Feb. 17, 2017, 4 Pages.
Patent Owner's Preliminary Response to U.S. Pat. No. 9,059,532, Dec. 27, 2016. 86 Pages.
Response to Opposition for European U.S. Pat. No. 2584962, Nov. 23, 2015, 154 Pages.
"Disposable and Accessories Catalog for Respiratory Diagnostics", CareFusion, Natus Medical Inc., 2009, 138 Pages.
Petition for Inter Partes Review of U.S. Pat. No. 9,059,532, Sep. 15, 2016.
International Search Report from PCT Application No. PCT/IS2010/000007, dated Oct. 1, 2010.
"Defendant's Fourth Supplemental Invalidity and Unenforceability Contentions," Nox Medical ehf v. Natus Neurology Inc., Civil Action No. 1:15-cv-00709-RGA, Mar. 22, 2017, 214 Pages.
"Natus Neurology Inc.'s Combined (1) Reply Brief in Support of Its Motion for Summary Judgment of Invalidity, (2) Brief in Opposition to Nox's Cross-Motion for Summary Judgment of No Invalidity, and (3) Brief in Opposition to Nox's Proposed Claim Constructions," Nox Medical ehf v. Natus Neurology Inc., Civil Action No. 1:15-cv-00709-RGA, Aug. 15, 2017, 416 Pages.
Statement Setting out the Grounds of Appeal from EP Application No. 11758266.8, Mar. 22, 2018, 62 Pages.
Final Written Decision, Inter Partes Review, Natus Medical Inc., Natus Neurology Inc., Embla Systems LLC, and Embla Systems LTD., Petitioner, v. Nox Medical ehf for U.S Pat. No. 9,059,532, Mar. 21, 2018, 39 Pages.
Patent Owner's Response Under 37 C.F.R 42.120, for U.S. Pat. No. 9,059,532, Jun. 29, 2017, 238 Pages.
Petitioners' Reply Pursuant to 37 C.F.R 42.23 (Redacted-Public Version), for U.S. Pat. No. 9,059,532, Oct. 9, 2017, 38 Pages.
Memorandum Opinion from Civil Action No. 15-709-RGA, Nox Medical ehf v. Natus Neurology Inc., Feb. 13, 2018, 24 Pages.
Judgment from Civil Action No. 15-709-RGA, Nox Medical ehf v. Natus Neurology Inc., May 8, 2018, 1 Page.
Plaintiff Nox Medical's Combined (1) Brief in Opposition to Natus' Motion for Summary Judgment of Invalidity, (2) Opening Brief in Support of Nox Medical's Cross-Motion for Summary Judgment of No Invalidity, and (3) Opening Brief in Support of Nox Medical's Proposed Claim Constructions from Civil Action No. 15-709-RGA, Nox Medical ehf v. Natus Neurology Inc., Jul. 26, 2017, 63 Pages.
Plaintiff Nox Medical EHF's Reply Brief in Further Support of Its Cross-Motion for Summary Judgment of No Invalidity from Civil Action No. 15-709-RGA, Nox Medical ehf v. Natus Neurology Inc., Aug. 23, 2017, 18 Pages.
Order from Civil Action No. 15-709-RGA, Nox Medical ehf v. Natus Neurology Inc., Feb. 13, 2018, 1 Page.
Verdict Form from Civil Action No. 15-709-RGA, Nox Medical ehf v. Natus Neurology Inc., May 7, 2018, 2 Pages.

Natus Neurology Inc.'s Brief in Support of Summary Judgment of Invalidity of the Asserted Claims of U.S. Pat. No. 9,059,532 from Civil Action No. 1:15-709-RGA, Nox Medical ehf v. Natus Neurology Inc., Jul. 7, 2017, 24 Pages.
Minutes of OP and Interlocutory Decision from Application No. 11 758 266.8, Nov. 6, 2017.
Notification of Minutes and Amendments at OP from Application No. 11 758 266.8, dated Nov. 6, 2017.
OP Decision and Reasoning from Application No. 11 758 266.8, Nov. 6, 2017.
Opposition against EP Application No. 11758266.8, Dec. 16, 2015.
Letter containing Test Results from European Patent No. 2584962, Feb. 23, 2017.
Escobar et al., "Nu-Way Snaps and Snap Leads: an Important Connection in the History of Behavior Analysis," Behav Analyst, 2014, vol. 37, pp. 95-107.
Declaration of Mr. Ami Vilhjalmsson, Apr. 11, 2017, 3 Pages.
Declaration of Mr. Hilmarsson, Apr. 6, 2017, 1 Page.
Declaration of Ms. Erna Sif Amardottir, 1 Page, Apr. 21, 2017.
Agustsson et al., "White Paper RIP Signal Assessment," Apr. 21, 2017, 21 Pa.
Statement of Mr. Sveinbjorn Hoskuldsson, Apr. 24, 2017, 2 Pages.
Statement from Mr. Andres Einar Hilmarsson, Apr. 24, 2017, 1 Page.
Declaration of Ms. Erla S. Amadottir, Apr. 25, 2017. 5 Pages.
Dehkordi et al., "Monitoring Torso Acceleration for Estimating the Respiratory Flow and Efforts for Sleep Apnea Detection," 34th Annual International Conference of the IEEE EMBS, Aug. 28, 2012, pp. 6345-6348.
International Search Report and Written Opinion from PCT Application No. PCT/IB2017/055022, dated Nov. 17, 2017.
International Search Report from PCT Application No. PCT/IB2017/053128, dated Aug. 9, 2017.
De Groote et al., "Mathematical Assessment of Qualitative Diagnostic Calibration for Respiratory Inductive Plethysmorgraphy," Journal of Applied Physiology, vol. 90, 2001, pp. 1025-1030.
Konno et al., "Measurement of the Separate Volume Changes of Rib Cage and Abdomen During Breathing," Journal of Applied Physiology, vol. 22, No. 3, 1967, pp. 407-422.
Sackner et al., "Calibration of Respiratory Inductive Plethysmograph During Natural Breathing," Journal of Applied Physiology, vol. 66, No. 1, 1989, pp. 410-420.
Augousti et al., "Comparative Analysis of the Isovolume Calibration Method for Non-Invasive Respiratory Monitoring Techniques Based on Area Transduction Versus Circumference Transduction Using the Connected Cylinders Model," Physiological Measurement, vol. 32, 2011, pp. 1265-1274.
International Search Report and Written Opinion from PCT Application No. PCT/IB2018/056892, dated Dec. 13, 2018.
Agha et al., "Facial Phenotype in Obstructive Sleep Apnea-Hypopnea Syndrome: A Systematic Review and Meta-Analysis," Journal of Sleep Research, vol. 26, 2017, pp. 122-131.
Agrawal et al., "Sound Frequency Analysis and the Site of Snoring in Natural and Induced Sleep," Clinical Otolaryngology, vol. 27, 2002, pp. 162-166.
Akoumianaki et al., "The Application of Esophageal Pressure Measurement in Patients with Respiratory Failure," American Journal of Respiratory and Critical Care Medicine, vol. 189, No. 5, Mar. 1, 2014, pp. 520-531.
Arnardottir et al., "Snoring—Validation of Different Objective Measurements," European Respiratory Society Annual Congress 2013, 1 Page.
Arnardottir et al., "How to Measure Snoring? A Comparison of the Microphone, Cannula and Piezoelectric Sensor," Journal of Sleep Research, vol. 25, 2016, pp. 158-168.
Arnardottir et al., "Obstructive Sleep Apnoea in the General Population: Highly Prevalent but Minimal Symptoms," European Respiratory Journal, vol. 47, 2016, pp. 194-202.
Ayappa et al., "Non-Invasive Detection of Respiratory Effort-Related Arousals (RERAs) by a Nasal Cannula/Pressure Transducer System," SLEEP, vol. 23, No. 6, 2000, pp. 763-771.

(56) References Cited

OTHER PUBLICATIONS

Berry et al., "Use of Chest Wall Electromyography to Detect Respiratory Effort During Polysomnography," Journal of Clinical Sleep Medicine, vol. 12, No. 9, 2016, pp. 1239-1244.
Berry et al., "AASM Scoring Manual Updates for 2017 (Version 2.4)," Journal of Clinical Sleep Medicine, vol. 13, No. 5, 2017, pp. 665-666.
Bloch et al., "Breathing Pattern During Sleep Disruptive Snoring," European Respiratory Journal, vol. 10, 1997, pp. 576-586.
Capistrano et al., "Facial Morphology and Obstructive Sleep Apnea," Dental Press Journal of Orthodontics, vol. 20, No. 6, Nov. 2015, pp. 60-67.
Eckert et al., "Pathophysiology of Adult Obstructive Sleep Apnea," Proceedings of the American Thoracic Society, vol. 5, 2008, pp. 144-153.
Faber et al., "Available Techniques for Objective Assessment of Upper Airway Narrowing in Snoring and Sleep Apnea," Sleep and Breathing, vol. 7, No. 2, 2003, pp. 77-86.
Ghafarian et al., "A Review on Human Respiratory Modeling," Tanaffos, vol. 15, No. 2, 2016, pp. 61-69.
Guilleminault et al., "Variability of Respiratory Effort in Relation to Sleep Stages in Normal Controls and Upper Airway Resistance Syndrome Patients," Sleep Medicine, vol. 2, 2001, pp. 397-406.
Harris et al., "GPCR Signalling in Hypertension: Role of GRKs," Clinical Science, vol. 115, 2008, pp. 79-89.
Heinzer et al., "Prevalence of Sleep-Disordered Breathing in the General Population: the HypnoLaus Study," Lancet Respiratory Medicine, vol. 3, No. 4, Apr. 2015, pp. 310-318.
Huo et al., "Endoscopic Upper Airway Evaluation in Obstructive Sleep Apnea: Mueller's Maneuver Versus Simulation of Snoring," Sleep Breath, vol. 19, 2015, pp. 661-667.
Konno et al., "Measurement of the Separate Volume," Journal of Applied Physiology, vol. 22, No. 3, 1967, pp. 407-422.
Kushida et al., "Technical Protocol for the use of Esophageal Manometry in the Diagnosis of Sleep-Related Breathing Disorders," Sleep Medicine, vol. 3, 2002, pp. 163-173.
Lee et al., "Energy Types of Snoring Sounds in Patients with Obstructive Sleep Apnea Syndrome: A Preliminary Observation," PLOS ONE, vol. 7, No. 12, Dec. 2012, 11 Pages.
Luo et al., "Diaphragm Electromyography Using an Oesophageal Catheter: Current Concepts," Clinical Science, vol. 115, 2008, pp. 233-244.
Masa et al., "Apnoeic and Obstructive Nonapnoeic Sleep Respiratory Events," European Respiratory Journal, vol. 34, 2009, pp. 156-161.
Otis et al., "Mechanical Factors in Distribution of Pulmonary Ventilation," Journal of Applied Physiology, vol. 8, No. 4, Jan. 1956, pp. 427-443.
Peppard et al., "Increased Prevalence of Sleep-Disordered Breathing in Adults," American Journal of Epidemiology, vol. 177, No. 9, Apr. 14, 2013, pp. 1006-1014.
Spinowitz et al., "Patterns of Upper Airway Obstruction on Drug-Induced Sleep Endoscopy in Patients with Sleep-Disordered Breathing with AHI < 5," American Academy of Otolaryngology—Head and Neck Surgery, 2017, 6 Pages.
Terrill et al., "Quantifying the Ventilatory Control Contribution to Sleep Apnoea Using Polysomnography," European Respiratory Journal, vol. 45, 2015, pp. 408-418.
Vandenbussche et al., "Assessment of Respiratory Effort During Sleep: Esophageal Pressure Versus Noninvasive Monitoring Techniques," Sleep Medicine Reviews, vol. 24, 2015, pp. 28-36.
Wellman et al., "A Method for Measuring and Modeling the Physiological Traits Causing Obstructive Sleep Apnea," Journal of Applied Physiology, vol. 110, 2011, pp. 1627-1637.
Wilson, "Compartmental Models of the Chest Wall and the Origin of Hoover's Sign," Respiratory Physiology & Neurobiology, vol. 210, 2015, pp. 23-29.
Duarte, "Detect Peaks in Data Based on Their Amplitude and Other Features.," retrieved from https://github.com/demotu/BMC/blob/master/functions/detect_peaks.py on Jun. 1, 2018, Oct. 3, 2014, 3 Pages.
Jones et al., "SciPy: Open Source Scientific Tools for Python," requested from http://www.scipy.org on Jun. 4, 2018, 2001, 3 Pages.
Orphanidou et al., "Signal-Quality Indices for the Electrocardiogram and Photoplethysmogram: Derivation and Applications to Wireless Monitoring," IEEE Journal of Biomedical and Health Informatics, vol. 19, No. 3, May 2015, pp. 832-838.
Roebuck et al., "A Review of Signals Used in Sleep Analysis," Physiological Measurement, vol. 35, 2014, pp. R1-R57.
International Search Report from PCT Application No. PCT/IB2018/053993, dated Aug. 24, 2018.
Lester et al., ""Are You With Me?"—Using Accelerometers to Determine if Two Devices are Carried by the Same Person," PERVASIVE, 2004, pp. 33-50.
Nino et al., "Robust Spectral Analysis of Thoraco-Abdominal Motion and Oxymetry in Obstructive Sleep Apnea," 35th Annual International Conference of the IEEE EMBS, Jul. 3, 2013, pp. 2906-2910.

* cited by examiner

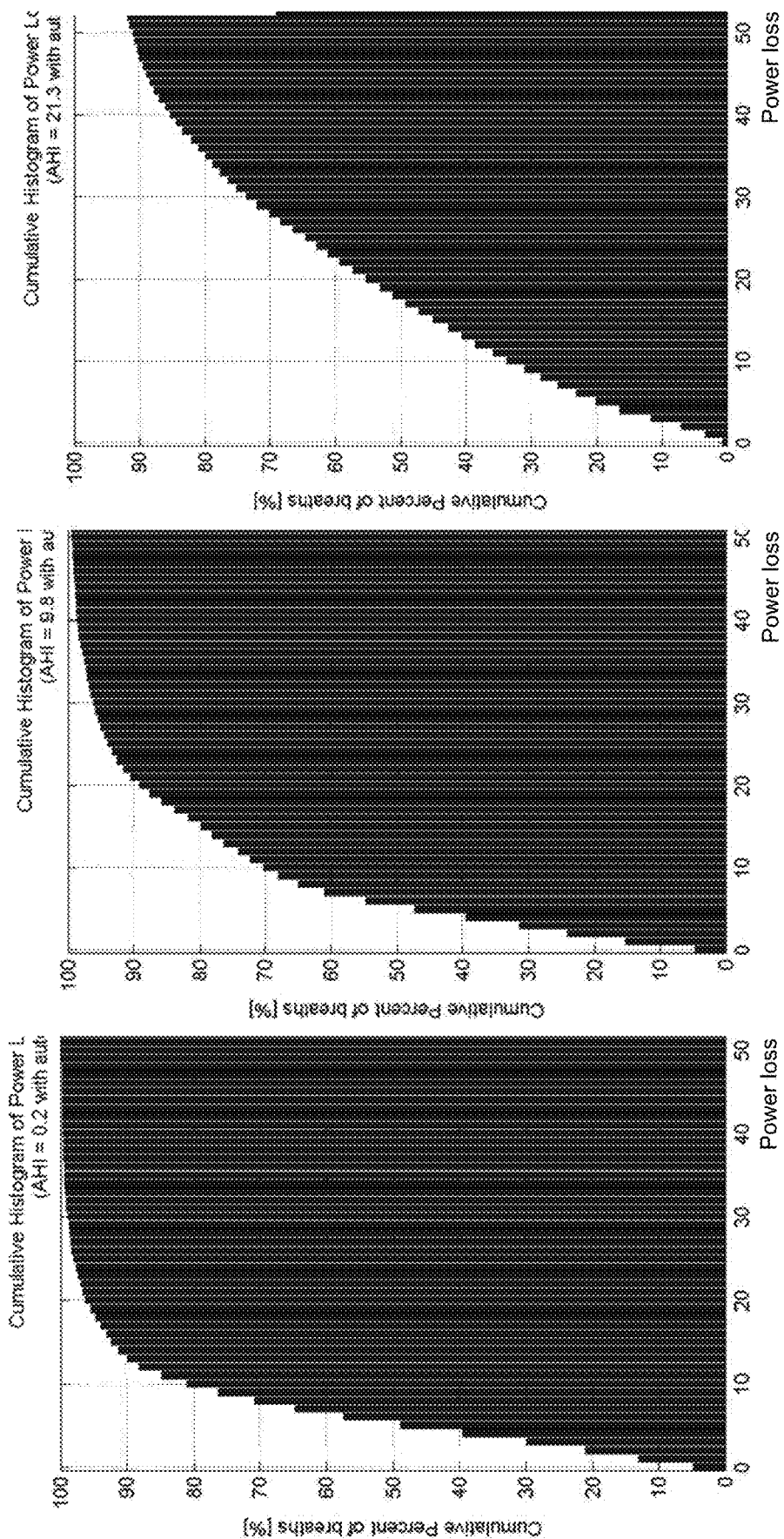

METHOD, APPARATUS, AND SYSTEM FOR MEASURING RESPIRATORY EFFORT

FIELD OF THE DISCLOSURE

The present disclosure relates to a method, apparatus, and system for measuring respiratory effort of a subject, and to a method, apparatus, and system for calculating a calibration factor for calibrating signals representative of the respiratory effort of a subject.

BACKGROUND

Non-invasive methods are useful and popular to measure breathing movements and respiratory effort. Respiratory Inductive Plethysmography (RIP) is one such method, which includes the use of respiratory bands to measure respiratory effort related areal changes. RIP technology includes a measurement of an inductance of a conductive belt or belts that encircles a respiratory region of a subject.

The signal amplitude received from the respiratory effort belts depends on both the shape of the subject and the placement of the belts. To create a respiration volume signal by summing the signal of the respiratory effort belts, one must use correct weighting constants for the measured belt signals to transform each signal correctly into a volume signal before summing them together. Further, to perform a quantitative calibration, the signals of the respiratory effort belts must be measured simultaneously with a quantitative reference measure. Known methods therefore require quantitative equipment for respiratory volume measure, such as a spirometer, body-box or similar ways to measure respiratory volume accurately during the calibration.

Due to the complexity added with using reference respiratory volume equipment and the fact that the weighting constants are subject to change over time with belt and body movements, it would simplify the measurement of respiratory efforts considerably if there were a method available that would evaluate weighting constants without the need of special quantitative equipment for reference measures.

Statistical measures of RIP during normal breathing to evaluate weighting constants may be used for respiratory analysis and sleep diagnostics. However, the calculation of a calibration factor will change if the belts move or the subject changes position. To maintain accuracy, recalibration is needed after such movements and changes, which requires a few minutes of normal, non-obstructive breathing. This can be difficult with a sleeping subject, especially with subject's suffering from sleep disordered breathing.

A method for calculating and calibrating the respiratory signals in a more continuous fashion without the need for quantitative equipment would be advantageous.

SUMMARY

The present disclosure concerns a method, apparatus, and system for measuring respiratory effort of a subject. According to one example, the method includes obtaining a thorax effort signal (T). The thorax effort signal (T) being an indicator of a thoracic component of the respiratory effort. An abdomen effort signal (A) is obtained, the abdomen effort signal (A) being an indicator of an abdominal component of the respiratory effort. The thorax effort signal (T) is separated into a volume-contributing thoracic component ($V_{ST}$) and a thoracic paradox component ($P_T$). The thoracic paradox component ($P_T$) represents a non-volume-contributing thoracic component of the respiratory effort, and the volume-contributing thoracic component ($V_{ST}$) representing a volume-contributing component of the respiratory effort. The abdomen effort signal (A) is separated into a volume-contributing abdominal component ($V_{SA}$) and an abdomen paradox component ($P_A$). The abdomen paradox component ($P_A$) represents a non-volume-contributing abdominal component of the respiratory effort, and the volume-contributing abdominal component ($V_{SA}$) represents a volume-contributing component of the respiratory effort. The non-volume-contributing abdominal component ($P_A$) is negatively proportional to the non-volume-contributing thoracic component ($P_T$). The thorax effort signal (T) is weighted by a weight factor $k_T$ and the abdomen effort signal (A) is weighted by a weight factor $k_A$ to obtain a volume-proportional signal ($V_{Sw}$). The volume-proportional signal ($V_{Sw}$) being proportional to the actual respiratory volume of the respiratory effort. The weight factors $k_T$ and $k_A$ are optimized by minimizing the non-volume-contributing thoracic component ($P_T$) and the non-volume-contributing abdominal component ($P_A$) in the resulting volume-proportional signal ($V_{Sw}$). In another embodiment, a calibration factor for calibrating the thorax effort signal (T) and the abdomen effort signal (A) may be obtained based on the optimized weight factors $k_T$ and $k_A$. According to another embodiment, a power loss parameter that is useful to predict respiration efficiency may also be determined based on the optimized weight factors $k_A$ and $k_T$ by comparing the amplitude of $V_{Sw}$ to the sum of the amplitudes of the weighted thorax effort signal T and the weighted abdomen effort signal A.

Also described herein is a hardware storage device having stored thereon computer executable instructions which, when executed by one or more processors, implement a method of measuring respiratory effort of a subject. According to one example, the method includes separating a received thorax effort signal (T) into a volume-contributing thoracic component ($V_{ST}$) and a thoracic paradox component ($P_T$). The thorax effort signal (T) is an indicator of a thoracic component of the respiratory effort, and the thoracic paradox component ($P_T$) represents a non-volume-contributing thoracic component of the respiratory effort. The volume-contributing thoracic component ($V_{ST}$) represents a volume-contributing component of the respiratory effort. An abdomen effort signal (A) is separated into a volume-contributing abdominal component ($V_{SA}$) and an abdomen paradox component ($P_A$). The abdomen effort signal (A) is an indicator of an abdominal component of the respiratory effort. The abdomen paradox component ($P_A$) represents a non-volume-contributing abdominal component of the respiratory effort, and the volume-contributing abdominal component ($V_{SA}$) represents a volume-contributing component of the respiratory effort. The non-volume-contributing abdominal component ($P_A$) is negatively proportional to the non-volume-contributing thoracic component ($P_T$). The thorax effort signal (T) is weighted by a weight factor $k_T$ and the abdomen effort signal (A) is weighted by a weight factor $k_A$ to obtain a volume-proportional signal ($V_{Sw}$). The volume-proportional signal ($V_{Sw}$) being proportional to the actual respiratory volume of the respiratory effort. The weight factors $k_T$ and $k_A$ are optimized by minimizing the non-volume-contributing thoracic component ($P_T$) and the non-volume-contributing abdominal component ($P_A$) in the resulting volume-proportional signal ($V_{Sw}$). In another embodiment, a calibration factor for calibrating the thorax effort signal (T) and the abdomen effort signal (A) may be obtained based on the optimized weight factors $k_T$ and $k_A$. According to another embodiment, a power loss parameter that is useful to predict respiration efficiency may also be determined based on the optimized weight factors $k_A$ and $k_T$ by comparing the amplitude of $V_{Sw}$ to the sum of the amplitudes of the weighted thorax effort signal T and the weighted abdomen effort signal A.

In another embodiment, a respiratory effort measuring system is described. The system includes a first sensor device configured to obtain a thorax effort signal (T), the thorax effort signal (T) being an indicator of a thoracic component of the respiratory effort, a second sensor device configured to obtain an abdomen effort signal (A), the abdomen effort signal (A) being an indicator of an abdominal component of the respiratory effort, and a processor configured to receive the thorax effort signal (T) and the abdomen effort signal (A). The processor separates the thorax effort signal (T) into a volume-contributing thoracic component ($V_{ST}$) and a thoracic paradox component ($P_T$), the thoracic paradox component ($P_T$) representing a non-volume-contributing thoracic component of the respiratory effort, and the volume-contributing thoracic component ($V_{ST}$) representing a volume-contributing component of the respiratory effort. The processor separates the abdomen effort signal (A) into a volume-contributing abdominal component ($V_{SA}$) and an abdomen paradox component ($P_A$), the abdomen paradox component ($P_A$) representing a non-volume-contributing abdominal component of the respiratory effort, and the volume-contributing abdominal component ($V_{SA}$) representing a volume-contributing component of the respiratory effort, wherein the non-volume-contributing abdominal component ($P_A$) is negatively proportional to the non-volume-contributing thoracic component ($P_T$). The thorax effort signal (T) is weighted by a weight factor $k_T$ and the abdomen effort signal (A) is weighted by a weight factor $k_A$ to obtain a volume-proportional signal ($V_{Sw}$). The volume-proportional signal ($V_{Sw}$) being proportional to the actual respiratory volume of the respiratory effort. The weight factor $k_T$ and $k_A$ are optimized by minimizing the non-volume-contributing thoracic component ($P_T$) and the non-volume-contributing abdominal component ($P_A$) in the resulting volume-proportional signal ($V_{Sw}$). In another embodiment, a calibration factor for calibrating the thorax effort signal (T) and the abdomen effort signal (A) may be obtained based on the optimized weight factors $k_T$ and $k_A$. According to another embodiment, a power loss parameter that is useful to predict respiration efficiency may also be determined based on the optimized weight factors $k_A$ and $k_T$ by comparing the amplitude of $V_{Sw}$ to the sum of the amplitudes of the weighted thorax effort signal T and the weighted abdomen effort signal A.

In another embodiment, a method of measuring respiratory effort of a subject is provided. The method includes obtaining a first effort signal, the first effort signal being an indicator of a first component of the respiratory effort. A second effort signal is obtained, the second effort signal being an indicator of a second component of the respiratory effort. The first effort signal is separated into a first volume-contributing component and a first paradox component, the first paradox component representing a non-volume-contributing of the first effort signal component of the respiratory effort, and the first volume-contributing component representing a first volume-contributing component of the respiratory effort. The second effort signal is separated into a second volume-contributing component and a second paradox component, the second paradox component representing a non-volume-contributing of the second effort signal component of the respiratory effort, and the second volume-contributing component representing a second volume-contributing component of the respiratory effort. The first non-volume-contributing component is negatively proportional to the second non-volume-contributing component. The first effort signal is weighted by a first weigh factor $k_1$ and the second effort signal is weighted by a second weight factor $k_2$ to obtain a volume-proportional signal, the volume-proportional signal being proportional to the actual respiratory volume of the respiratory effort. The weight factors $k_1$ and $k_2$ are optimized by minimizing the first non-volume-contributing component and the second non-volume-contributing component in the resulting volume-proportional signal ($V_{Sg}$). In another embodiment, a calibration factor for calibrating the first and the second effort signals may be obtained based on the optimized weight factors $k_1$ and $k_2$. Or, a power loss may be determined based on the optimized first or second weight factor ($k_1$ and $k_2$). According to another embodiment, a power loss parameter that is useful to predict respiration efficiency may also be determined based on the optimized weight factors $k_1$ and $k_2$ by comparing the amplitude of $V_{Sg}$ to the sum of the amplitudes of the weighted first effort signal and the weighted second effort signal.

BRIEF DESCRIPTION OF THE DRAWINGS

FIGS. 4a, 4b, and 4c, respectively, show a cumulative and relative histograms for power loss in 3 subjects with different levels of upper airway obstruction, from left, (a) subject 1: AHI 0.2, (b) subject 2: AHI 9.8, and (c) subject 3: AHI 21.3.

DETAILED DESCRIPTION OF VARIOUS EMBODIMENTS

Non-invasive methods to measure breathing movements and respiratory effort may include the use of respiratory effort bands or belts placed around the respiratory region of a subject. The sensor belt may be capable of measuring either changes in the band stretching or the area of the body encircled by the belt when placed around a subject's body. A first belt may be placed around the thorax and second belt may be placed around the abdomen to capture respiratory movements caused by both the diaphragm and the intercostal-muscles. When sensors measuring only the stretching of the belts are used, the resulting signal is a qualitative measure of the respiratory movement. This type of measurement is used for example for measurement of sleep disordered breathing and may distinguish between reduced respiration caused by obstruction in the upper airway (obstructive apnea), where there can be considerable respiratory movement measured, or if it is caused by reduced effort (central apnea), where reduction in flow and reduction in the belt movement occur at the same time.

Unlike the stretch sensitive respiratory effort belts, areal sensitive respiratory effort belts provide detailed information on the actual form, shape and amplitude of the respiration taking place. If the areal changes of both the thorax and abdomen are known, by using a certain calibration technology, the continuous respiratory volume can be measured from those signals and therefore the respiratory flow can be derived.

Figure 2:
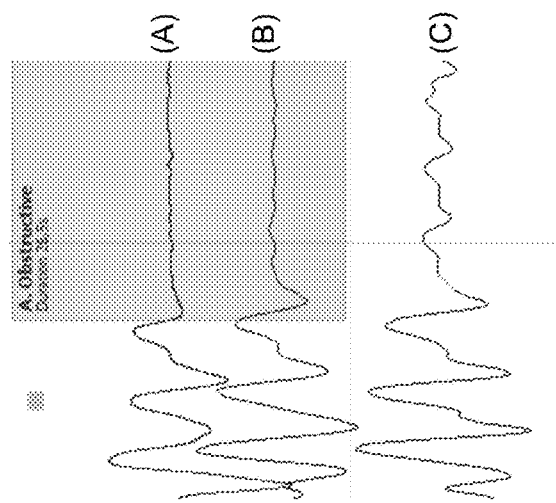
FIG. 2 illustrates a reference flow signal (top), a flow signal from calibrated RIP sum (middle), and flow signal derived from uncalibrated RIP signals (bottom).
Figure 1B:
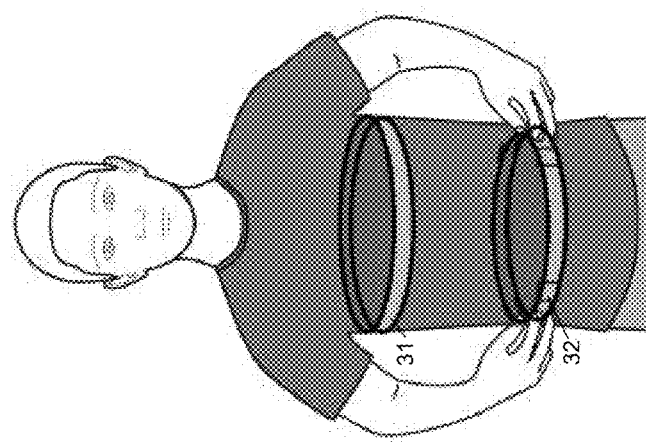
FIGS. 1a and 1b illustrate an example of respiratory inductance plethysmograph (RIP) belts, 1a shows an example of the wave-shaped conductors in the belts, 1b shows the cross-sectional area of each belt, which is proportional to the measured inductance.
Figure 1A:
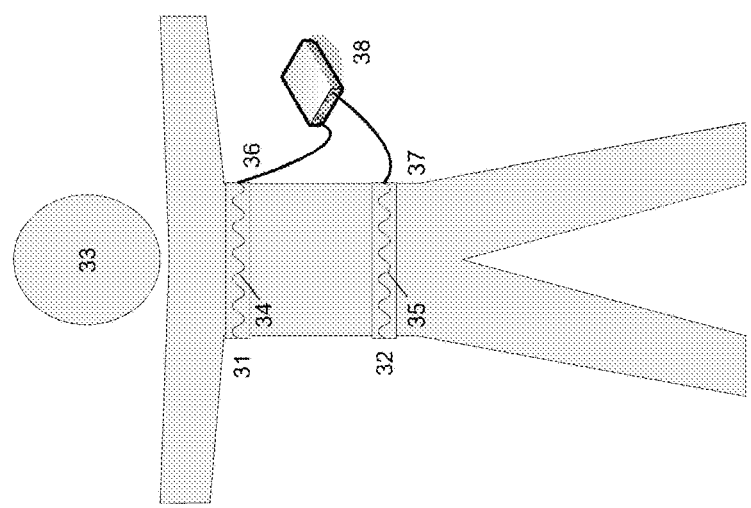
Figure 3:
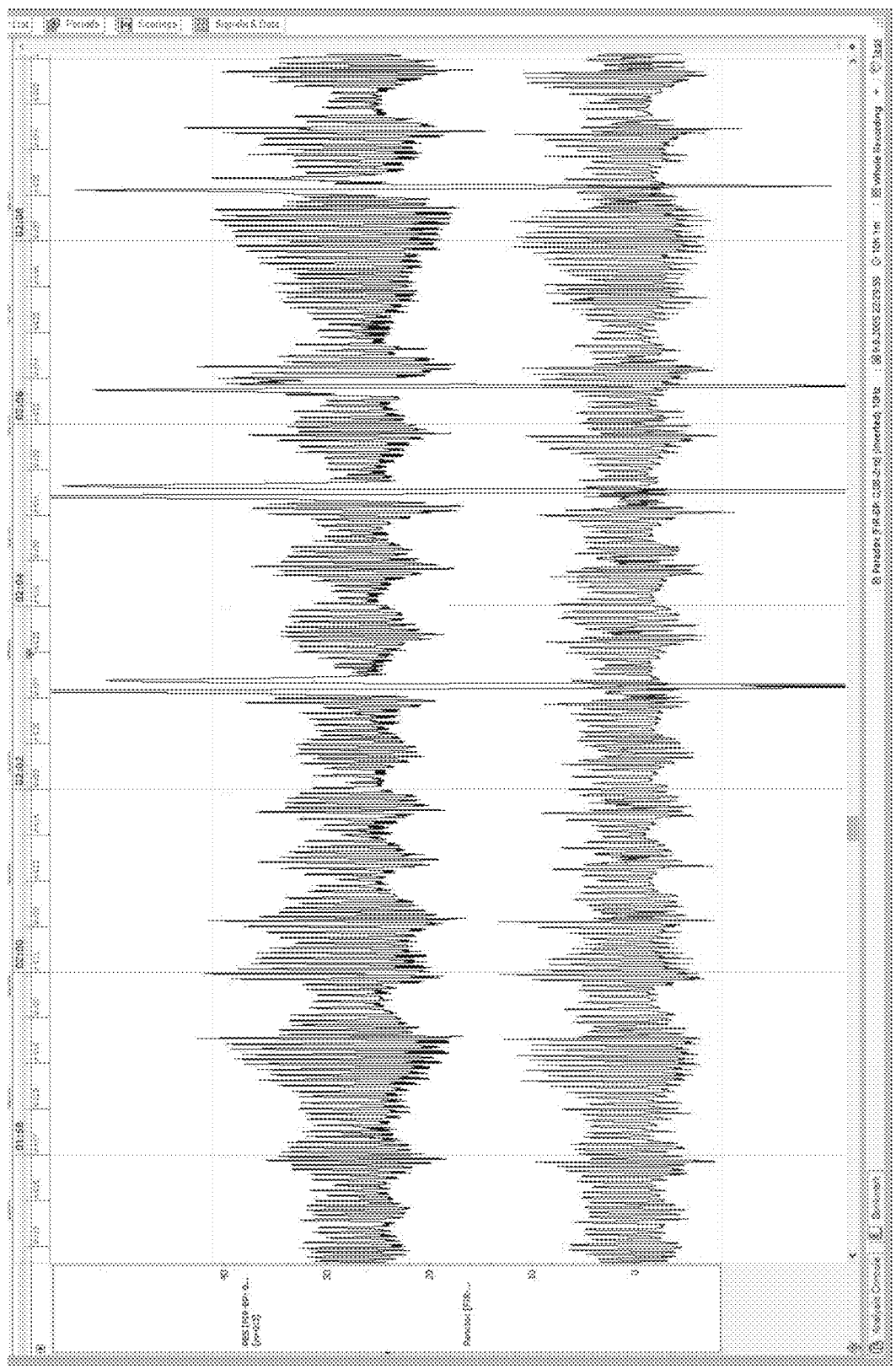
FIG. 3 shows a comparison between measured esophageal pressure (top) and a non-volume contributing effort signal (bottom) derived from RIP signals.

Respiratory Inductive Plethysmography (RIP) is a method to measure respiratory related areal changes. As shown in FIG. 1, in RIP, belts 31, 32 may contain a conductor 34, 35 that when put on a subject 33, form a conductive loop that creates an inductance that is directly proportional to the absolute cross sectional area of the body part that is encircled by the loop. When such a belt is placed around the abdomen or thorax, the cross sectional area is modulated with the respiratory movements and therefore also the inductance of the belt. Conductors 34, 35 may be connected to signal processor 38 by leads 36, 37. Processor 38 may include a memory storage. By measuring the belt inductance, a value is obtained that is modulated directly proportional with the respiratory movements. RIP technology includes therefore an inductance measurement of conductive belts that encircle the thorax and abdomen of a subject.

In another embodiment, conductors may be connected to a transmission unit that transmits respiratory signals, for example raw unprocessed respiratory signals, or semi-processed signals, from conductors to processing unit. Respiratory signals or respiratory signal data may be transmitted to the processor by hardwire, wireless, or by other means of signal transmission.

Resonance circuitry may be used for measuring the inductance and inductance change of the belt. In a resonance circuit, an inductance L and capacitance C can be connected together in parallel. With a fully charged capacitor C connected to the inductance L, the signal measured over the circuitry would swing in a damped harmonic oscillation with the following frequency:

$$f = \frac{1}{2\pi\sqrt{LC}}, \quad (1)$$

until the energy of the capacitor is fully lost in the circuit's electrical resistance. By adding to the circuit an inverting amplifier, the oscillation can however be maintained at a frequency close to the resonance frequency. With a known capacitance C, the inductance L can be calculated by measuring the frequency f and thereby an estimation of the cross-sectional area can be derived.

The signal amplitude received from the respiratory effort belts depends on both the shape of the subject and the placement of the belts. The thorax respiration signal may be approximately the same for the whole thorax region but the areal change may be differently proportional to the thorax respiration signal, depending on where on the thorax the belt is placed and how the subject is shaped.

The same may be true for the abdomen region. The abdomen respiration signal may be driven by the diaphragm alone and therefore may be the same all over the abdomen region, but depending on where the belt is located and the shape of the abdomen, the areal change may be differently proportional to the abdomen respiration signal.

To create a respiration volume signal by summing the thorax respiration and abdomen respiration, one must therefore use the correct weights for the measured belt signals to transform each signal correctly into a volume signal before summing them together.

If the thorax RIP signal is T and the abdomen RIP signal is A the total volume signal can be represented as:

$$V_R = k_V(k_t \times T + (1-k_t) \times A) \quad (2),$$

where $k_t$ is the weight of the thorax signal towards the abdomen signal and the $k_V$ is the gain required to change the weighted belt sum to the actual $V_R$ measured in liters or other volume unit.

To perform a quantitative calibration, the signals T and A must be measured simultaneously with a quantitative reference measure of $V_R$. Based on the result, the constants, $k_V$ and $k_t$ can be derived using methods such as least square fitting. This method does therefore require quantitative equipment for respiratory volume measure, such as a spirometer, body-box or similar ways to measure $V_R$ accurately during the calibration.

Even if the quantitative measure of $V_R$ is of interest, e.g. for pulmonary function tests, it is sufficient for many applications to derive a signal that is only proportional to the actual volume. This is the case in sleep monitoring, where the purpose with the measure is to detect abnormal breathing patterns, generally by determining if the amplitude of one breath deviates from a reference breath. In this case it is sufficient to evaluate the proportion between the thorax and abdomen signals before summing, that is, for a volume proportional sum $V_{S1}$, $$V_{S1} = (k_T \times T + (1-k_T) \times A) \quad (3).$$

As one of skill in the art would understand, due to the linearity of the system, as the absolute gain of the signal is not relevant, the weight factor for T can be changed to any value as long as the weight factor for A is changed proportionally. A simplified presentation of the above equation can therefore be used for the sake of argument, where $k_T = 1$ and $k_A = (1-k_T)/k_T$ resulting in the equation:

$$V_S = (T + k_A \times A) \quad (4.1).$$

Due to the complexity added with using reference respiratory volume equipment and the fact that the $k_A$ is a subject to change over time with belt and body movements, it would simplify the measure considerably if there would be a method available that would evaluate $k_A$ without the need of a special equipment for reference measures.

A method may use statistical measures of RIP during normal breathing to evaluate $k_A$, using an algorithm referred to as Qualitative Diagnostic Calibration (QDC).

The QDC algorithm allows a qualitative calibration of the RIP signals during normal breathing to estimate the $k_A$ without the use of a reference volume signal. The method is based on the findings that during normal breathing (non-obstructive), the variance in the amplitude of the thorax and abdomen RIP signals, when correctly calibrated should be the same, given that the tidal volume of the breaths are approximately the same. By measuring a number of breaths (e.g. for a 5 minute period), selecting the breaths that are close to being normal distributed around the average tidal volume and calculating the standard deviation of the selected breaths for the thorax signal (Sd(T)) and abdomen signals (Sd(A)), the gain factor can be evaluated as follows:

$$k_A = \frac{Sd(T)}{Sd(A)}. \quad (5)$$

This method may be useful for respiratory analysis and sleep diagnostics. The drawback is however that the $k_A$ will change if the belts move or the subject changes position. To maintain accuracy, recalibration is needed after such movements and changes, and that requires a few minutes of normal, non-obstructive breathing. This can be difficult with a sleeping subject, especially with subject's suffering from sleep disordered breathing. Preferably, a calibration factor for the respiratory signals would be obtainable in a more continuous fashion.

The underlying model and parameters of a preferable method are herein described. For a calibrated system the following applies:

From equation (3.1) $V_S=(T+k_AA)$ (3.2),

As explained above, due to the linearity of the system, other weight factors for $k_T$ and $k_A$ have the same effect, such as choosing to set the weight factor $k_A$ to be equal to one ($k_A=1$), arriving at equation (3.3) below, and $k_T$ may be determined as the weight factor, which may be defined as the ration of weights for T towards A.

$$V_{S2}=(k_TT+A) \quad (3.3)$$

Furthermore, both Thorax and Abdomen could have weights other than 1 resulting in $$V_{Sw}=(k_TT+k_AA) \quad (3.4),$$

For ease in understanding the model, in the description below, the weight factor $k_T$ is, however, chosen to be equal to one ($k_T=1$). Based on equation (3.2), the following may be further defined:

$$T=k_{VT} \times V_S+P \quad (6),$$

$$k_AA=(1-k_{VT}) \times V_S-P \quad (7).$$

In the above formulas $k_{VT}$ is the contribution of the thorax movement, in the range from 0 to 1 to the volume sum $V_S$, whereas the remaining contribution of $(1-k_{VT})$ must come from the abdomen movement. The product of $k_{VT} \times V_S$ is therefore the flow-contributing component of T while $(1-k_{VT}) \times V_S$ is the flow-contributing component of A. The residual movement of the thorax, T may be termed herein as a paradox component P and is the exact opposite of a paradox movement in $k_AA$. Therefore by summing the two, the P and -P cancel the effect of each other, as this movement is not contributing any respiratory volume.

In the extreme case of almost non-obstructive breathing, the P close to zero and the shape of both T and $k_AA$ is close to be identical to $V_S$, $$T=k_{VT} \times V_S \text{ and } k_AA=(1-k_{VT}) \times V_S.$$

During the other extreme case of fully obstructive breathing, $V_S$ drops to zero, T=P while $k_AA=-P$.

The model may therefore successfully describe respiratory movements of thorax and abdomen for differing levels of obstruction, given that the coefficients, $k_A$ and $k_{VT}$ are known. Further, a calibration factor for calibrating the thorax effort signal T and the abdomen effort signal A may be obtained based on the optimized weight factor $k_A$. The weight factor coefficients $k_A$ and $k_{VT}$ may then be stored, and the calibrated thorax effort signal T and the abdomen effort signal A and the volume sum $V_S$ may be stored and displayed on a display device.

From equations (5) and (6) an equation for the parameter P can be derived:

$$P=T-k_{VT}V_S \quad (8).$$

As can be seen in equation (7) above, the paradox signal cannot be determined from the T, $k_AA$ and $V_S$ only but is also a function of the actual volume contribution from each belt $k_{VT}$.

In accordance with the model of this embodiment, there are different ways to suitably determine the coefficients $k_A$ and $k_{VT}$, some examples of which are described herein.

Amplitude and Power Loss Due to Summing of Channels

As $V_S$ is the sum of the volume-contributing components of the thorax and abdomen signals, the paradox components present in T and $k_AA$ disappear in the sum. As part of the signal is lost, the amplitude of the summed signal $V_S$ is therefore less than the sum of the amplitudes of T and $k_AA$, and the same is true for the power of the summed signal $V_S$ as compared to the sum of the powers of T and $k_AA$. (In this context, 'power' refers to mathematical power function, not electrical power.) Thus, based on equation (3), $V_S=(T+k_AA)$, it follows that for the amplitude, the following applies:

$$|V_S| \leq |T|+|k_AA| \quad (9),$$

and therefore its power is as follows:

$$P\langle V_S \rangle \leq P\langle T \rangle + P\langle k_AA \rangle. \quad (10).$$

This power loss is minimal during normal breathing, increases with increased partial obstruction until it is absolute during complete obstruction. For any given timeframe, the amplitude and power loss are at maximum when the sum is correctly calibrated. Accordingly, a useful $k_A$ value can be obtained which is a value that maximizes the power loss and/or amplitude loss, compared with the sum of the power or amplitudes respectively, of T and A over a period of time. This is done in certain useful embodiments of the disclosure and readily achieved with iterative calculations.

Paradox Present in Higher Frequencies

Obstructive changes in the airway during a single breath are by nature quicker events than the respiration itself and do therefore contain higher frequency components compared with the flow signal. The power of P is therefore more in the higher frequencies compared with $V_S$ and the relative power of the fundamental frequency is therefore higher in $V_S$ than in both T and $k_AA$.

Accordingly, in some embodiments a useful $k_A$ value is obtained, by finding a $k_A$ value such that the proportional power of lower frequencies in the respiratory signal is maximized as compared with higher frequencies in the respiratory signal, over a period of time. It is apparent that "lower" and "higher" frequencies in this context are determined based on normal breathing frequencies. Thus lower frequencies could be, in one embodiment, frequencies lower than double the average frequency being measured (which is generally the fundamental frequency of the breathing signal, readily determined, e.g. by FT transforming of the signal). Or in other embodiments frequencies lower than 1 Hz, 0.5 Hz or lower, such as lower than 0.2 Hz (12 breathes per minute) or lower than 0.1 Hz. Higher frequencies would accordingly be those frequencies that are higher than the cutoff between lower and higher frequencies, or in some embodiments those frequencies that are higher than the fundamental frequency of the breathing signal.

Based on the above, the present disclosure further provides for, in some embodiments, ways to use the magnitude of the loss of amplitude or power, the magnitude of loss of the higher frequency components or a combination of these to determine a $k_A$ value that is considered optimal over a certain period of time.

Maximum Fundamental Frequency Optimization (MFF)

In another embodiment, a MFF method seeks by trial and error over a certain period, the $k_A$ that results in the $V_S=(T+k_AA)$ that maximizes the power of the fundamental frequency of the signal relative to the overall signal power. The logic is that as P contains higher frequency components than $V_S$, maximizing the relative power of the fundamental frequency is the same as minimizing the effects of P in the sum.

The MFF method is applied in useful embodiments. The fundamental frequency is generally the undisturbed breathing rhythm, the period referred to can be relatively short, such as but not limited to breath by breath (one breathing cycle), or a predetermined period such as 1 min or a few minutes. Different time-frequency analysis methods can be used separately or together for maximizing of the method efficiency, including but not limited to, Wavelet transform, Fourier transformation, statistical modeling, etc.

Minimum Signal Amplitude Optimization (MSA)

A MSA method seeks by trial and error for a given period the $k_A$ that results in the $V_S=(T+k_A A)$ that minimizes the resulting signal compared with the amplitude of T and $k_A A$, $$S_l \min = \min\left(\frac{RMS(V_S)}{RMS(T)+RMS(k_A A)}\right). \quad (11)$$

$S_l$ can be understood as relative difference between the $V_S$ amplitude versus the sum of the amplitudes of T and $k_A A$. The logic is that P contributes to the amplitude of the measured signal but not to the amplitude of the respiration. By minimizing the amplitude of the resulting signal $S_l$, one is minimizing the influence of P and the respiration part of the signal is therefore maximized. The period in the MSA method can in some embodiments be the period of a single breath (suitably determined as described above), or a few breaths, or longer, such as in the range from about 10 sec. to about 10 minutes, such as e.g. about 0.5 minute, or about 1 min period, about 5 minutes or about 10 min period. In other embodiments longer periods are used, such as 0.5 hour, 1 hour, or a period of a few hours (e.g. 2, 3, 4 or 5 hours), where a suitable period can be selected depending on the application.

Minimum Obstruction Amplitude (MOA) Optimization

The MOA method is useful for periods of time in embodiments where there are quick changes in the signal amplitudes between breaths and periods of obstruction. The obstructive periods provide the opportunity to perform conventional isovolume calibration, by selecting the $k_A$ that minimizes in the best way the $V_S$ during obstruction. This can be done for a period of the signal (e.g. 0.5 minute, or 1 min or a few minutes such as in the range 1-5 minutes), by dividing the period into a number of n shorter time frames of few seconds each (such as e.g. in the range of 3-10 seconds, or in the range of 3-5 seconds; should fit within an apnea). For a given timeframe i, the $S_l \min(i)$ is found and the relative $k_A(i)$ is stored. The value of $k_A$ for the whole period (longer period) is then selected by a weighted average over the period by giving the timeframes that resulted in the lowest $S_l$min values the maximum weight. More weight can be given to the timeframes that performed in the best way by using a non-linear weight transformation.

In some embodiments, combinations of two or more of the above methods are applied to obtain a suitable optimal $k_A$ value.

In other embodiments one or more method as described above is applied to derive an intermediate $k_A$ value for a shorter time span, such as e.g. in the range of 5-60 seconds, such as 5-30 seconds, or in the range 5-20 seconds, or in the range 10-30 seconds, and weighing the performance for each timespan and choosing a $k_A$ for the longer timespan (e.g. in the range 1-15 minutes, or in the range 1-10 minutes, such as 5-10 minutes, or longer time spans such as in the range 10-60 minutes, or in some embodiments even longer periods, such as in the range 1-10 hours, e.g. in the range 1-5 hours or in the range 5-10 hours), based on selecting the method providing the most determinant result.

For evaluating and deriving a suitable determinant value of the weighing ratio, various methods can be applied. In one embodiment the performance of the intermediate periods and intermediate values is evaluated by weighing the performance for each intermediate time span (e.g. averaging or otherwise statistically comparing), then the different methods can be compared by comparing which method(s) gives a most consistent value with minimal fluctuations while maintaining the minimal paradoxical components.

Weighting in the Neighboring Periods

The method reliability is in some embodiments enhanced further by selecting a set of periods and basing the selection of $k_{Aj}$ on an average, weighted sum or other performance criteria from the periods in the set. In this way, an accurate $k_{Aj}$ value can be selected for periods that have low signal and frequency magnitude losses, based on a more reliable estimation of a neighboring period.

This is in some embodiments done, e.g., by splitting each minute (or other chosen time span) into overlapping intermediate periods (e.g. 5 seconds, or intermediate periods of other chosen time length, such as but not limited to 3 seconds, 8, or 10 seconds), the $k_{Aj}$ value used for the whole time span can be the weighted sum of the $k_A$ values for each intermediate period where the weight of the periods that have the maximum amplitude/power loss and/or frequency loss is higher than for periods that show lower losses. This can then be applied for longer periods, taking a set of time spans (e.g., minute time spans) and for example calculating a weighted trend-curve for the changes of $k_A$ minute by minute, giving the minutes with the strongest losses the maximum weight and those with low losses the minimum weight.

Selecting an Optimization Method

To adapt optimally to the information available at each period in the signal, the method should preferably use the $k_A$ that fits best for each condition. The measure of how well a method performs can be based on the quantity of the amplitude, signal or frequency loss, where the method providing the highest loss is generally considered the optimal one.

A good criteria for selecting the $k_A$ also preferably results in less switching between methods and optimally that switching from one method to the other occurs when the two methods predict nearly the same value of $k_A$. This way a continuous trend is achieved where sudden shifts in the resulting signal are avoided, caused by switching methods.

To further optimize the selection criteria, a good result can be achieved by processing a series of periods instead of one by one and then choosing the methods for each period that maximizes the continuity of the $k_A$ between periods, minimizes the number of switches between methods or a combination of both.

Signals Derived from the Calibrated Effort

A number of interesting and useful signals can be derived with the embodiments of this disclosure, from the calibrated thorax and abdomen signals.

The Paradox P and the Thorax Volume Contribution $k_{VT}$

As demonstrated in equation (7), even after optimally calibrating the sum, the level of the paradox signal P has more than one solution depending on the $k_{VT}$.

To evaluate the P, a method must be created to seek for the correct $k_{VT}$. The physiological characteristics of P is that the paradox is driven by the pressure difference in the Thorax and in the surrounding atmosphere, caused by the inhalation of air over a partial obstruction in the upper airway. For a given pressure difference, the paradox status generally has a balance to the lowest energy level capable of creating that status. This characteristic can be used to determine a useful and correct value P by choosing the $k_{VT}$ that results in the lowest power function/amplitude of P. Accordingly, in a further embodiment, this disclosure provides a method for determining a useful value of the paradox component P.

The paradox signal P is of special interest as it is directly derived from the thorax internal pressure and is a strong indication of the respiratory effort taking place for each breath. This parameter is a candidate for being used as a substitute for a very invasive method currently being used in sleep medicine. This method is direct measure of the esophageal pressure that is currently performed by threading a catheter through the nose and into the esophageal to monitor the respiratory pressure below the upper airway obstruction.

The other signal is the thorax contribution that is also of interest as the physiology suggests that the ratio of thorax contribution vs. abdomen contribution changes with the level of sleep, the respiratory muscular activity being different during REM sleep compared with the S1, S2 and S3. Sudden changes in the contribution ratio are therefore strongly related with REM onset and offset.

The Power Loss Ratio

As described in equations (8) and (9) the total amplitude and thus the power of the sum $V_S$ is less than the sum of the amplitude and power of the T and $k_A A$ due to the loss of the paradox signal P.

The value $S_i$min defined in (10) describes the efficiency of the respiration, that is, what portion of the respiratory movement did result in respiratory flow and what portion did not. This index is of great interest as it predicts in a continuous manner the quality of the breathing, being 100% during no obstruction to become 0% for total obstruction or the other way around, the power loss being 0% for no obstruction and 100% for full obstruction.

As this index is the same as is used to seek the calibration value $k_A A$, it can also be calculated directly from the belt signals by applying the model defined in (10), seeking the $k_A$ that results in the minimum $S_i$min and use that value as a power loss index. FIGS. 5a, 5b, and 5c show cumulative and relative histograms of power loss in three subjects with different breathing. As can be seen the histograms are quite different, illustrating difference between subjects with healthy breathing and subjects with disordered breathing. Using 20% power loss as a threshold, only 5% of the breaths of Subject 1 are above that threshold, 20% of the breaths of Subject 2 and half of the breaths of Subject 3. The power loss index is therefore a candidate to be used as a quantitative measure of the level of partial obstruction.

Volume Calibration and Stabilization

As can be seen from equations (2) and (3), $V_R$ is an absolute volume signal measured in liters, while $V_S$ is a signal that is directly proportional to $V_R$ but is not the absolute volume signal. If the sensitivity of T changes in (3) due to belt movement or other changes in physiology, the gain between $V_S$ and $V_R$ changes during the night. This causes the problem for signal like the $V_S$ and P that even if their initial values where known in a volume unit like liters, they would change or drift through the night. This can be prevented to some degree by fixing the belts as tightly to the subject as possible. However, if there were a biomedical parameter that would allow the belts to be regulated to show a constant ratio towards $V_R$ the results would allow the signals to be used with confidence to compare amplitudes at different times over the night.

The present disclosure provides a further method that makes use of the physiological characteristics that the human body regulates the intake of oxygen to match the need of the cells at all time, not building up or dropping oxygen levels during normal breathing. The indication of increased metabolism is higher minute ventilation (minute ventilation referring to the total volume inspired or expired per minute) and heart rate and during aerobic breathing the ratio between minute ventilation and heart rate is close to linear. The method monitors the relative minute ventilation from the $V_S$ signal and compares it to a measured heart rate. The characteristic linearity between the minute ventilation and heart rate is captured during periods where the $k_A$ is not changing significantly but where there is a variation in the minute ventilation and heart rate. The captured value is then used to correct the $V_S$ when there is a change in the $k_A$ values. This way the $V_R/V_S$ ratio can be kept nearly constant throughout the recording, allowing volume calibration to take place at one or more points during the recording and delivering reliable measure for all periods.

Certain terms are used throughout the description and claims to refer to particular methods, features, or components. As those having ordinary skill in the art will appreciate, different persons may refer to the same methods, features, or components by different names. This disclosure does not intend to distinguish between methods, features, or components that differ in name but not function. The figures are not necessarily to scale. Certain features and components herein may be shown in exaggerated scale or in somewhat schematic form and some details of conventional elements may not be shown or described in interest of clarity and conciseness.

Although various example embodiments have been described in detail herein, those skilled in the art will readily appreciate in view of the present disclosure that many modifications are possible in the example embodiments without materially departing from the concepts of present disclosure. Accordingly, any such modifications are intended to be included in the scope of this disclosure. Likewise, while the disclosure herein contains many specifics, these specifics should not be construed as limiting the scope of the disclosure or of any of the appended claims, but merely as providing information pertinent to one or more specific embodiments that may fall within the scope of the disclosure and the appended claims. Any described features from the various embodiments disclosed may be employed in combination. In addition, other embodiments of the present disclosure may also be devised which lie within the scopes of the disclosure and the appended claims. Each addition, deletion, and modification to the embodiments that falls within the meaning and scope of the claims is to be embraced by the claims.

Certain embodiments and features may have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges may appear in one or more claims below. Any numerical value is "about" or "approximately" the indicated value, and takes into account experimental error and variations that would be expected by a person having ordinary skill in the art.

What is claimed:

1. A method of measuring respiratory effort of a subject, the method comprising:

obtaining a thorax effort signal (T), the thorax effort signal (T) being an indicator of a thoracic component of the respiratory effort, the thorax effort signal (T) including a volume-contributing thoracic component ($V_{ST}$) and a thoracic paradox component ($P_T$), the thoracic paradox component ($P_T$) representing a non-volume-contributing thoracic component of the respiratory effort, and the volume-contributing thoracic component ($V_{ST}$) representing a volume-contributing component of the respiratory effort;

obtaining an abdomen effort signal (A), the abdomen effort signal (A) being an indicator of an abdominal component of the respiratory effort, the abdomen effort signal (A) including a volume-contributing abdominal component ($V_{SA}$) and an abdomen paradox component ($P_A$), the abdomen paradox component ($P_A$) representing a non-volume-contributing abdominal component of the respiratory effort, and the volume-contributing abdominal component ($V_{SA}$) representing a volume-contributing component of the respiratory effort, wherein the abdominal paradox component ($P_A$) is negatively proportional to the thoracic paradox component ($P_T$); and performing a calibration of the thorax effort signal (T) and the abdomen effort signal (A) based on the obtained thorax effort signal (T) and the abdomen effort signal (A) by weighting the thorax effort signal (T) by a first weight factor ($k_T$) and weighting the abdomen effort signal (A) by a second weight factor ($k_A$) to obtain a volume-proportional signal ($V_{Sw}$), the volume-proportional signal ($V_{Sw}$) being proportional to the actual respiratory volume of the respiratory effort;

calculating a ratio between an amplitude or power, or a transformation function of the amplitude or power of the volume-proportional signal ($V_{Sw}$) and a sum of the amplitudes, power, or a transformation function of the thorax effort signal (T) weighted by the first weight factor ($k_T$) and the abdomen effort signal (A) weighted by the second weight factor ($k_A$); and selecting the first and second weight factors ($k_T$ and $k_A$) that minimize said calculated ratio.

2. The method according to claim 1, wherein
the second weight factor ($k_A$) is set to be equal to one,
the first weight factor ($k_T$) is set to be equal to one, or
wherein the first weight factor ($k_T$) is set such that $k_T = 1 - k_A$.

3. The method according to claim 1, further comprising calculating a respiratory flow proportional signal ($F_S$) by calculating a first derivative of the volume-proportional signal ($V_{Sw}$).

4. The method according to claim 1, further comprising obtaining a calibration factor by reiteratively performing said calibration of the thorax effort signal (T) and the abdomen effort signal (A) over a plurality of time spans including a first timespan within a second time span, the first time span being shorter than the second time span; and selecting a calibration ratio for the second time span based on an obtained calibration factor of the plurality of time spans that provides a most determinant result.

5. The method according to claim 1, further comprising selecting a value for the first and second weight factors ($k_T$ and $k_A$) by determining intermediate values for weighing ratios for a set of a plurality of consecutive intermediate time spans and calculating the value for the first and second weight factors ($k_T$ and $k_A$) by weighing values within the set of time spans so as to maximize a continuity of weighed values over the set.

6. The method according to claim 1, wherein the thorax effort signal (T) is obtained by providing a first sensor device configured to measure the thoracic component of the respiratory effort of the subject, and the abdomen effort signal (A) is obtained by providing a second sensor device configured to measure the abdomen component of the respiratory effort of the subject.

7. The method according to claim 1, further comprising obtaining a measured heart rate of the subject and using said measured heart rate to determine another weight factor such that the volume proportional signal ($V_{Sw}$) is proportional to the actual respiratory volume of the respiratory effort throughout performance of the method even in a case that the patient changes position.

8. The method according to claim 1, wherein the calibration of the thorax effort signal (T) and the abdomen effort signal (A) is based only on the obtained the thorax effort signal (T) and the abdomen effort signal (A) without a quantitative reference measurement additional to the thorax effort signal (T) or the abdomen effort signal (A).

9. The method according to claim 1, further comprising determining a power loss based on the selected first and second weight factors ($k_T$ and $k_A$) that minimize said calculated ratio.

10. The method according to claim 9, further comprising evaluating flow resistance from the thoracic paradox component ($P_T$) or the abdomen paradox component ($P_A$) and a first derivative of the volume-proportion signal ($V_{Sw}$) with respect to time.

11. A method of measuring respiratory effort of a subject, the method comprising:

obtaining a thorax effort signal (T), the thorax effort signal (T) being an indicator of a thoracic component of the respiratory effort, the thorax effort signal (T) including a volume-contributing thoracic component ($V_{ST}$) and a thoracic paradox component ($P_T$), the thoracic paradox component ($P_T$) representing a non-volume-contributing thoracic component of the respiratory effort, and the volume-contributing thoracic component ($V_{ST}$) representing a volume-contributing component of the respiratory effort;

obtaining an abdomen effort signal (A), the abdomen effort signal (A) being an indicator of an abdominal component of the respiratory effort, the abdomen effort signal (A) including a volume-contributing abdominal component ($V_{SA}$) and an abdomen paradox component ($P_A$), the abdomen paradox component ($P_A$) representing a non-volume-contributing abdominal component of the respiratory effort, and the volume-contributing abdominal component ($V_{SA}$) representing a volume-contributing component of the respiratory effort, wherein the abdominal paradox component ($P_A$) is negatively proportional to the thoracic paradox component ($P_T$);

performing a calibration of the thorax effort signal (T) and the abdomen effort signal (A) based on the obtained thorax effort signal (T) and the abdomen effort signal (A) by weighting the thorax effort signal (T) by a first weight factor ($k_T$) and weighting the abdomen effort signal (A) by a second weight factor ($k_A$) to obtain a volume-proportional signal ($V_{Sw}$), the volume-proportional signal ($V_{Sw}$) being proportional to the actual respiratory volume of the respiratory effort; and optimizing the first and second weight factors ($k_T$ and $k_A$) by determining values for the first and second weight factors ($k_T$ and $k_A$) that maximize the power of lower frequencies in the volume proportional signal ($V_{Sw}$) compared to the power of higher frequencies in the volume proportional signal ($V_{Sw}$) over a period of time.

12. A method of measuring respiratory effort of a subject, the method comprising:

obtaining a thorax effort signal (T), the thorax effort signal (T) being an indicator of a thoracic component of the respiratory effort, the thorax effort signal (T) including a volume-contributing thoracic component ($V_{ST}$) and a thoracic paradox component ($P_T$), the thoracic paradox component ($P_T$) representing a non-volume-contributing thoracic component of the respiratory effort, and the volume-contributing thoracic component ($V_{ST}$) representing a volume-contributing component of the respiratory effort;

obtaining an abdomen effort signal (A), the abdomen effort signal (A) being an indicator of an abdominal component of the respiratory effort, the abdomen effort signal (A) including a volume-contributing abdominal component ($V_{SA}$) and an abdomen paradox component ($P_A$), the abdomen paradox component ($P_A$) representing a non-volume-contributing abdominal component of the respiratory effort, and the volume-contributing abdominal component ($V_{SA}$) representing a volume-contributing component of the respiratory effort, wherein the abdominal paradox component ($P_A$) is negatively proportional to the thoracic paradox component ($P_T$);

performing a calibration of the thorax effort signal (T) and the abdomen effort signal (A) based on the obtained thorax effort signal (T) and the abdomen effort signal (A) by weighting the thorax effort signal (T) by a first weight factor ($k_T$) and weighting the abdomen effort signal (A) by a second weight factor ($k_A$) to obtain a volume-proportional signal ($V_{Sw}$), the volume-proportional signal ($V_{Sw}$) being proportional to the actual respiratory volume of the respiratory effort; and deriving the thoracic paradox component ($P_T$) of the thorax effort signal (T) or the abdomen paradox component ($P_A$) of the abdomen effort signal (A), or a derivative of the thoracic paradox component ($P_T$) of the thorax effort signal (T) or the abdomen paradox component ($P_A$) of the abdomen effort signal (A)

by determining values for the first and second weight factors ($k_T$ and $k_A$) that minimize an amplitude or power of the volume proportional signal ($V_{Sw}$) compared to the sum of the powers of the thoracic effort signal weighted by the first weight factor ($k_T$) and the abdomen effort signal (A) weighted by the second weight factor ($k_A$) over a period of time.

13. The method according to claim 12, further comprising evaluating flow resistance from the thoracic paradox component ($P_T$) or the abdomen paradox component ($P_A$) and a first derivative of the volume-proportion signal ($V_{Sw}$) with respect to time.

14. A hardware storage device having stored thereon computer executable instructions which, when executed by one or more processors, implement a method of measuring respiratory effort of a subject comprising:

obtaining a thorax effort signal (T), the thorax effort signal (T) being an indicator of a thoracic component of the respiratory effort, the thorax effort signal (T) including a volume-contributing thoracic component ($V_{ST}$) and a thoracic paradox component ($P_T$), the thorax effort signal (T) being an indicator of a thoracic component of the respiratory effort, the thoracic paradox component ($P_T$) representing a non-volume-contributing thoracic component of the respiratory effort, and the volume-contributing thoracic component ($V_{ST}$) representing a volume-contributing component of the respiratory effort;

obtaining an abdomen effort signal (A), the abdomen effort signal (A) being an indicator of an abdominal component of the respiratory effort the abdomen effort signal (A) including a volume-contributing abdominal component ($V_{SA}$) and an abdomen paradox component ($P_A$), the abdomen effort signal (A) being an indicator of an abdominal component of the respiratory effort, the abdomen paradox component ($P_A$) representing a non-volume-contributing abdominal component of the respiratory effort, and the volume-contributing abdominal component ($V_{SA}$) representing a volume-contributing component of the respiratory effort, wherein the abdominal paradox component ($P_A$) is negatively proportional to the thoracic paradox component ($P_T$); and performing a calibration of the thorax effort signal (T) and the abdomen effort signal (A) based on the obtained thorax effort signal (T) and the abdomen effort signal (A) by weighting the thorax effort signal (T) by a first weight factor ($k_T$) and weighting the abdomen effort signal (A) by a second weight factor ($k_A$) to obtain a volume-proportional signal ($V_{Sw}$), the volume-proportional signal ($V_{Sw}$) being proportional to the actual respiratory volume of the respiratory effort;

calculating a ratio between an amplitude or power, or a transformation function of the amplitude or power of the volume-proportional signal ($V_{Sw}$) and a sum of the amplitudes, power, or a transformation function of the thorax effort signal (T) weighted by the first weight factor ($k_T$) and the abdomen effort signal (A) weighted by the second weight factor ($k_A$); and selecting the first and second weight factors ($k_T$ and $k_A$) that minimize said calculated ratio.

15. A respiratory effort measuring system comprising:

a first sensor device configured to obtain a thorax effort signal (T), the thorax effort signal (T) being an indicator of a thoracic component of the respiratory effort, the thorax effort signal (T) including a volume-contributing thoracic component ($V_{ST}$) and a thoracic paradox component ($P_T$), the thoracic paradox component ($P_T$) representing a non-volume-contributing thoracic component of the respiratory effort, and the volume-contributing thoracic component ($V_{ST}$) representing a volume-contributing component of the respiratory effort;

a second sensor device configured to obtain an abdomen effort signal (A), the abdomen effort signal (A) being an indicator of an abdominal component of the respiratory effort, the abdomen effort signal (A) including a volume-contributing abdominal component ($V_{SA}$) and an abdomen paradox component ($P_A$), the abdomen paradox component ($P_A$) representing a non-volume-contributing abdominal component of the respiratory effort, and the volume-contributing abdominal component ($V_{SA}$) representing a volume-contributing component of the respiratory effort, wherein the abdominal paradox component ($P_A$) is negatively proportional to the thoracic paradox component ($P_T$); and a processor configured to receive the thorax effort signal (T) and the abdomen effort signal (A);

wherein the processor performs a calibration of the thorax effort signal (T) and the abdomen effort signal (A) based on the obtained thorax effort signal (T) and the abdomen effort signal (A) by weighting the thorax effort signal (T) by a first weight factor ($k_T$) and weights the abdomen effort signal (A) by a second weight factor ($k_A$) to obtain a volume-proportional signal ($V_{Sw}$), the volume-proportional signal ($V_{Sw}$) being proportional to the actual respiratory volume of the respiratory effort;

calculating a ratio between an amplitude or power, or a transformation function of the amplitude or power of the volume-proportional signal ($V_{Sw}$) and a sum of the amplitudes, power, or a transformation function of the thorax effort signal (T) weighted by the first weight factor ($k_T$) and the abdomen effort signal (A) weighted by the second weight factor ($k_A$); and selecting the first and second weight factors ($k_T$ and $k_A$) that minimize said calculated ratio.

16. The respiratory effort measuring system according to claim 15, wherein the processor obtains a calibration factor by reiteratively performing said calibration of the thorax effort signal (T) and the abdomen effort signal (A) over a plurality of time spans including a first timespan within a second time span, the first time span being shorter than the second time span, and selecting a calibration ratio for the second time span based on an obtained calibration factor of the plurality of time spans that provides a most determinant result.

17. The respiratory effort measuring system according to claim 15, wherein the processor selects a value for the first and second weight factors ($k_T$ and $k_A$) by determining intermediate values for weighing ratios for a set of a plurality of consecutive intermediate time spans and calculating the value for the first and second weight factors ($k_T$ and $k_A$) by weighing values within the set of time spans so as to maximize a continuity of weighed values over the set.

18. A method of measuring respiratory effort of a subject, comprising:

obtaining a thorax effort signal (T), the thorax effort signal (T) being an indicator of a thoracic component of the respiratory effort, the thorax effort signal (T) including a volume-contributing thoracic component ($V_{ST}$) and a thoracic paradox component ($P_T$), the thoracic paradox component ($P_T$) representing a non-volume-contributing thoracic component of the respiratory effort, and the volume-contributing thoracic component ($V_{ST}$) representing a volume-contributing component of the respiratory effort;

obtaining an abdomen effort signal (A), the abdomen effort signal (A) being an indicator of an abdominal component of the respiratory effort, the abdomen effort signal (A) including a volume-contributing abdominal component ($V_{SA}$) and an abdomen paradox component ($P_A$), the abdomen paradox component ($P_A$) representing a non-volume-contributing abdominal component of the respiratory effort, and the volume-contributing abdominal component ($V_{SA}$) representing a volume-contributing component of the respiratory effort, wherein the abdominal paradox component ($P_A$) is negatively proportional to the thoracic paradox component ($P_T$);

performing a calibration of the thorax effort signal (T) and the abdomen effort signal (A) based on the obtained thorax effort signal (T) and the abdomen effort signal (A) by weighting the thorax effort signal (T) by a first weight factor ($k_T$) and weighting the abdomen effort signal (A) by a second weight factor ($k_A$) to obtain a volume-proportional signal ($V_{Sw}$), the volume-proportional signal ($V_{Sw}$) being proportional to the actual respiratory volume of the respiratory effort; and calculating a ratio between a transformation function of the volume-proportional signal ($V_{Sw}$) and a sum of a transformation function of the thorax effort signal (T) weighted by the first weight factor ($k_T$) and the abdomen effort signal (A) weighted by the second weight factor ($k_A$); and selecting the first and second weight factors ($k_T$ and $k_A$) that minimize said calculated ratio.

19. The method according to claim 18, wherein said selecting of the first and second weight factors ($k_T$ and $k_A$) includes optimizing the first and second weight factors ($k_T$ and $k_A$) by determining values for the first and second weight factors ($k_T$ and $k_A$) that maximize the power of lower frequencies in the volume proportional signal ($V_{Sw}$) compared to the power of higher frequencies in the volume proportional signal ($V_{Sw}$) over a period of time.

20. The method according to claim 18, wherein said selecting of the first and second weight factors ($k_T$ and $k_A$) includes optimizing the first and second weight factors ($k_T$ and $k_A$) by determining values for the first and second weight factors ($k_T$ and $k_A$) that minimize an amplitude or power of the volume proportional signal ($V_{Sw}$) compared to the sum of the powers of the thoracic effort signal weighted by the first weight factor ($k_T$) and the abdomen effort signal (A) weighted by the second weight factor ($k_A$) over a period of time.

* * * * *